United States Patent [19]
Dumoulin

[11] Patent Number: 5,406,377
[45] Date of Patent: Apr. 11, 1995

[54] SPECTROSCOPIC IMAGING SYSTEM USING A PULSED ELECTROMAGNETIC RADIATION SOURCE AND AN INTERFEROMETER

[75] Inventor: Charles L. Dumoulin, Ballston Spa, N.Y.

[73] Assignee: General Electric Company, Schenectady, N.Y.

[21] Appl. No.: 96,805

[22] Filed: Jul. 26, 1993

Related U.S. Application Data

[63] Continuation-in-part of Ser. No. 909,276, Jul. 6, 1992, abandoned.

[51] Int. Cl.$^6$ .............................................. G01B 9/02
[52] U.S. Cl. ................................... 356/346; 356/345; 356/359
[58] Field of Search ............... 356/345, 346, 359, 361, 356/376, 382, 360, 358, 357

[56] References Cited

U.S. PATENT DOCUMENTS 5,042,949 8/1991 Greenberg et al. ................. 356/359

OTHER PUBLICATIONS

U.S. Patent Application "Scanning Spectral Analysis Micro-probe Subsystem" by Charles L. Dumoulin, Serial No. 07/546,281 filed Jun. 29, 1990
"Optical Interferometry", by Glen M. Robinson, et al, Scientific American, Jul. 1991, pp. 445–449.

*Primary Examiner*—Samuel A. Turner
*Assistant Examiner*—LaCharles P. Keesee, II
*Attorney, Agent, or Firm*—Lawrence P. Zale; Marvin Snyder

[57] ABSTRACT

A pulsed electromagnetic radiation (EMR) source and an interferometer are used to obtain spectra from the surface of a sample. The pulsed EMR source uses a broadband radiation source and a monochromator to generate monochromatic radiation. Alternatively, a tunable laser can be used as the monochromatic radiation source. The modulated radiation impinges on the surface of interest where it is absorbed. The absorption of radiation causes the surface of the sample to expand. This change in dimension is then detected by an interferometer which employs a monochromatic radiation source to measure the instantaneous distance between the sample surface and the interferometer. The detection system of the interferometer can be an imaging device such as a video camera to obtain the spatial distribution of chemical composition of the sample surface.

14 Claims, 4 Drawing Sheets

SPECTROSCOPIC IMAGING SYSTEM USING A PULSED ELECTROMAGNETIC RADIATION SOURCE AND AN INTERFEROMETER

This is a continuation-in-part of Ser. No. 07/909,276 filed Jul. 6, 1992, now abandoned.

CROSS REFERENCE TO RELATED APPLICATIONS

This application is related to application "DUAL INTERFEROMETER SPECTROSCOPIC IMAGING SYSTEM", Ser. No. 07/909,277 filed Jul. 6, 1992, and "SPECTROSCOPIC IMAGING SYSTEM WITH ULTRASONIC DETECTION OF THE ABSORPTION OF MODULATED ELECTROMAGNETIC RADIATION" Ser. No. 07/909,275 both by Charles L. Dumoulin, both filed simultaneously with this application, and both assigned to the present assignee.

BACKGROUND OF THE INVENTION

1. Field of the Invention

The present invention relates to optical spectroscopy and more particularly to the optical spectroscopy of a surface of a sample.

2. Description of Related Art

Absorption and transmission spectra of a sample can be obtained using electromagnetic radiation for the purpose of identifying chemical types. Certain spectral regions are of greater use than others. The spectral regions of greatest use are those in which chemical species contained within the sample absorb radiation at characteristic wavelengths. The absorbed radiation can be detected directly, re-emitted by the sample or cause the sample to fluoresce. Spectroscopic measurements of absorption, emission and fluorescence using infra-red, visible and ultra-violet light are widely used for sample analysis. Unfortunately, many of these techniques are not well suited to applications where the sample has rough surfaces. Radiation is scattered by rough surfaces thereby making measurement of reflection difficult. Techniques requiring transmission through a sample are difficult or impossible using opaque samples.

One technique which has proved useful for the spectroscopic analysis of rough surfaces is Photo-Acoustic Spectroscopy. With this technique, a monochromatic light source is chopped to create a pulsed light source. The pulsed light is directed to impinge on the surface of the sample. The pulsed light is at a wavelength which is absorbed by the sample, causing a periodic heating of the surface which in turn causes the surface to expand and contract. This movement generates sound waves which propagate through the gas above the surface and are detected by a sensitive microphone. Spectra of the surface are generated by varying the wavelength of the incident radiation. Unfortunately, the detection efficiency of Photo-Acoustic procedures is low with respect to other optical analysis methods, and thus the technique is not easily applied to small samples.

A non-spectroscopic technique which has been demonstrated to be useful for the analysis of surface roughness is Optical Interferometry. In this technique, monochromatic light impinges upon a sample surface resulting in interferograms. The resulting interferograms are then used to generate digital maps of the surface. While this technique detects the physical features of a surface, it is not capable of providing information about the surface's chemical composition. A review of the techniques of optical interferometry of surfaces is described in *Optical Interferometry* Scientific American July 1991, pages 44–49 by Glen M. Robinson, Ph.D., David M. Perry, and Richard W. Peterson which is hereby incorporated by reference.

Presently there is a need for an analytical system capable of making a spectroscopic image indicating the distribution of selected chemical types, and the roughness of surfaces of samples with high sensitivity.

SUMMARY OF THE INVENTION

A spectroscopic imaging system according to the invention comprises a monochromatic pulsed electromagnetic radiation (EMR) source and an interferometer. The pulsed EMR source may be a tunable laser, or a broadband radiation source whose output energy is sent through a monochromator and interrupted at a pulsing frequency. The pulsed radiation impinges on a portion of the surface of the sample of interest where it is absorbed, causing the temperature of the surface to rise. This rise in temperature causes the surface to expand. Since the light is pulsed (i.e. the amplitude of the radiation varies with time) heating of the surface is periodic. This results in a periodic expansion and contraction of the surface material at the pulsing frequency.

An interferometer employing a continuous monochromatic light source is also used to illuminate the surface of the sample. Unlike the light source used to periodically expand the material at the surface, the wavelength of the continuous light source is chosen to minimize absorption of the light by the sample surface. The light from the continuous light source irradiates the portion of the surface irradiated by the pulsed EMR source and is reflected by the sample surface. The reflected light is used by the interferometer to create a two-dimensional interferogram which is stored for further use. An imaging device capable of detecting optical intensity at a plurality of spatial locations, such as a video camera, is used as the detection device to acquire the interferograms within the interferometer. At least three interferogram images are obtained each at a different light path distance when the sample is radiated with the pulsed EMR source and at least three more interferograms are obtained with no EMR pulsed source irradiation for corresponding light path distances. Since the distance between the surface and the interferometer changes in response to the pulsed EMR source, and since the magnitude of the response is proportional to the degree of absorption, the difference between corresponding interferograms (with and without EMR pulsed radiation at the same interferometer to sample surface distance) indicates locations of chemical absorption of the wavelength of EMR pulsed source. The differences interferograms may be combined to form a map of chemical types of the surface also indicating the.

OBJECTS OF THE INVENTION

It is an object of the invention to provide a system for obtaining absorption spectra from a rough surface of a sample.

It is another object of the invention to provide a system for obtaining surface roughness maps of a desired sample.

It is another object of the invention to provide a system for obtaining absorption spectra from a non-transparent sample.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
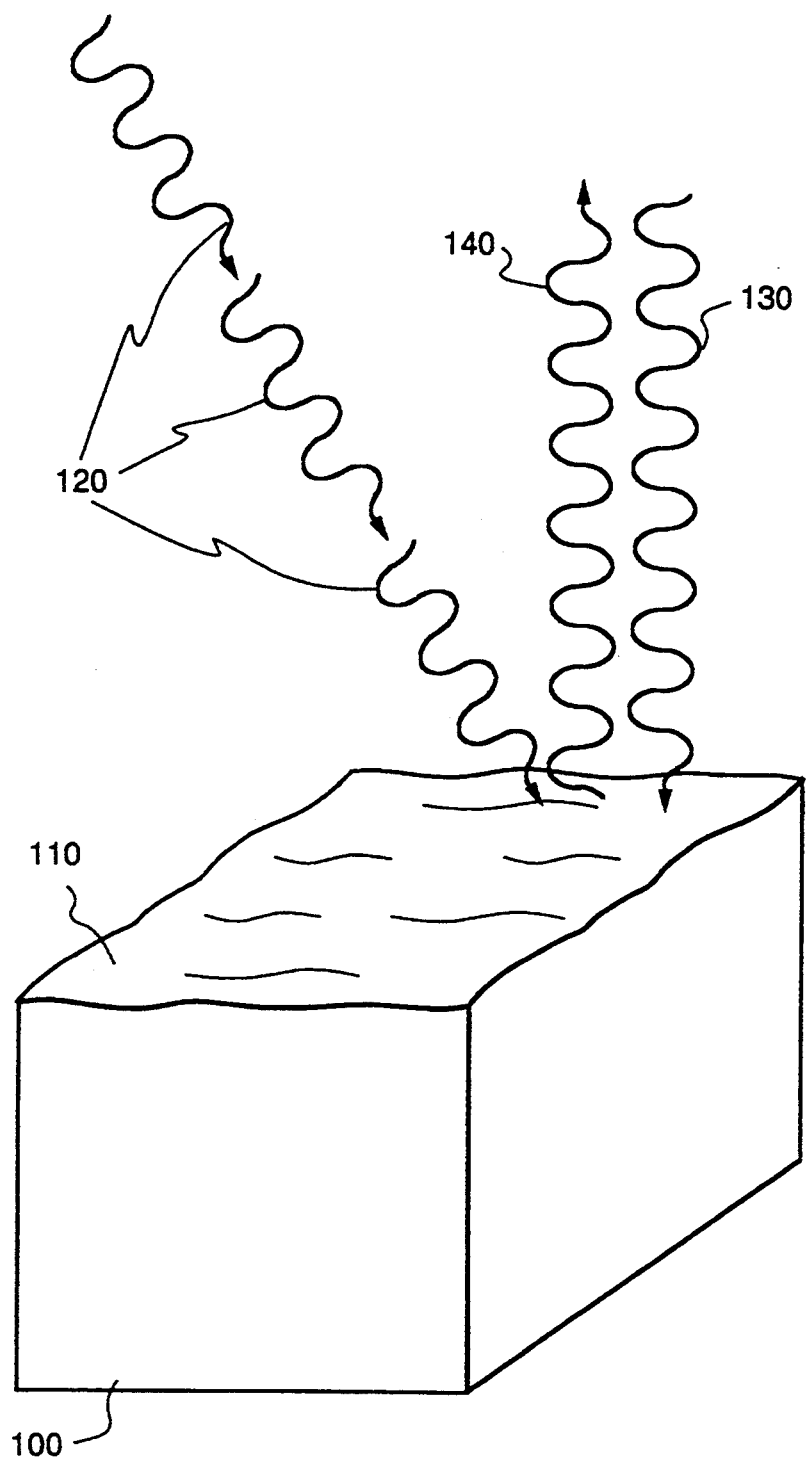
FIG. 1 is a perspective view of a sample surface absorbing radiation from one source and reflecting radiation from a second source.

FIG. 1 shows a sample 100 having a surface 110 to be analyzed. A sample excitation beam 120 of electromagnetic radiation from a pulsed electromagnetic radiation (EMR) source impinges upon a region of surface 110. An amount of sample excitation beam 120 is absorbed by surface 110 which is characteristic of specific chemical components.

A measurement beam 130 of monochromatic electromagnetic radiation from an interferometer impinges on the portion of surface 110 irradiated by sample excitation beam 120 and is reflected to produce a return beam 140 of electromagnetic radiation. The wavelength of the monochromatic source for measurement beam 130 is chosen to minimize absorption of this radiation by sample 100. Return beam 140 is scattered by the rough surface, but a sufficient amount of radiation is reflected back to an interferometer means 220 (shown in FIG. 2) where it is used to make an accurate measurement of the displacement of surface 110 with respect to interferometer means 220 by an interferogram. An interferogram is a spatial representation of optical intensity produced when two beams of radiation constructively and destructively interfere with each other.

Figure 2:
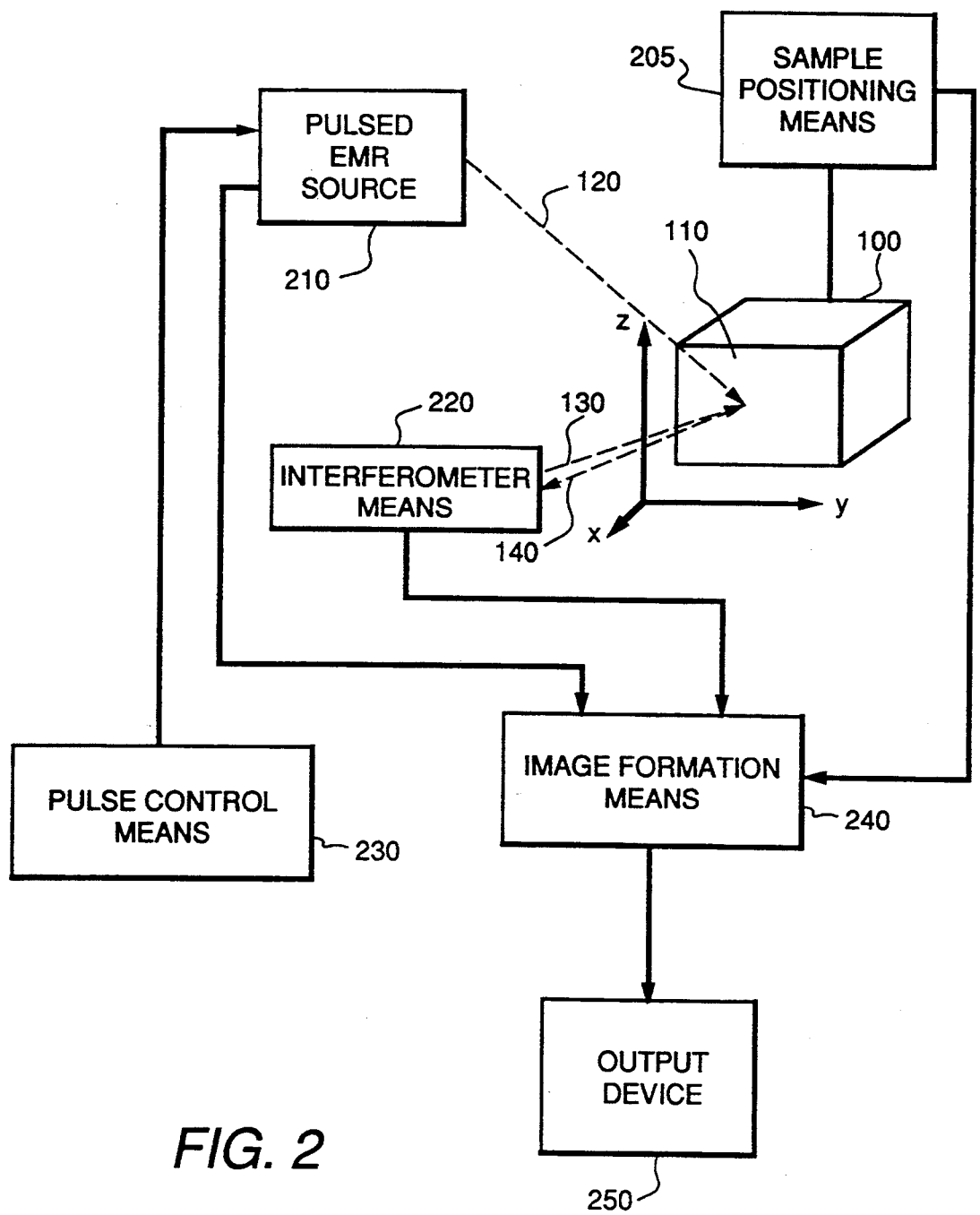
FIG. 2 is a block diagram of one embodiment of the present invention in which a pulsed electromagnetic radiation (EMR) source and an interferometer are used to obtain absorption spectra from a selected sample surface.

FIG. 2 is a schematic diagram of one embodiment of the present invention. Here, sample 100 is shown positioned at a desired location in three dimensions (x,y,z) relative to the system by a sample positioning means 205. A region of surface 110 of sample 100 is then irradiated by pulsed EMR source 210 at a specific wavelength while interferometer means 220 irradiates the same region of the sample surface. A pulse control means 230 is used to control the wavelength and modulation of pulsed EMR source 210. A signal indicating the wavelength and pulsing frequency from pulsed EMR source 210 is sent to an image formation means 240. Interferograms from interferometer means 220 are propagated to image formation means 240 substantially simultaneously with the signal from pulse control means 230. Signals indicating the position of sample 100 are sent from sample positioning means 205 to image formation means 240. Interferograms are also produced in the same manner from at least two additional effective distances between interferometer means 220 and sample surface 110. Corresponding interferograms are also produced by interferometer means 220 without pulsed EMR source 210 being active at the same effective distances.

Image formation means 240 computes a surface roughness image based upon the interferograms obtained without the need for additional scanning as described in the aforementioned Robinson et al. paper at pages 44–49, hereby incorporated by reference.

Image formation means 240 then subtracts intensities for each point of the surface roughness image obtained in the presence of electromagnetic radiation from pulsed EMR source 210 from its corresponding interferogram obtained at the same effective distance to determine at least three difference fields. Differences fields indicate motion of portions of the surface induced by absorption of radiation of pulsed EMR source 210. The greater the difference, the greater the absorption at that point to the wavelength used to irradiate the sample surface. Image formation means 240 then employs the signals provided by the pulsed EMR source 210, the interferometer means 220, and sample position means 205 to generate absorption data for a plurality of irradiated points on sample surface 110. If this is repeated for a plurality of pulsed EMR source wavelengths, an absorption spectrum for each point of sample surface 110 may be generated. By matching the absorption spectra against known absorption spectra, a chemical-type map may be generated across sample surface 110. This information may then be displayed on an output device 250.

Figure 3:
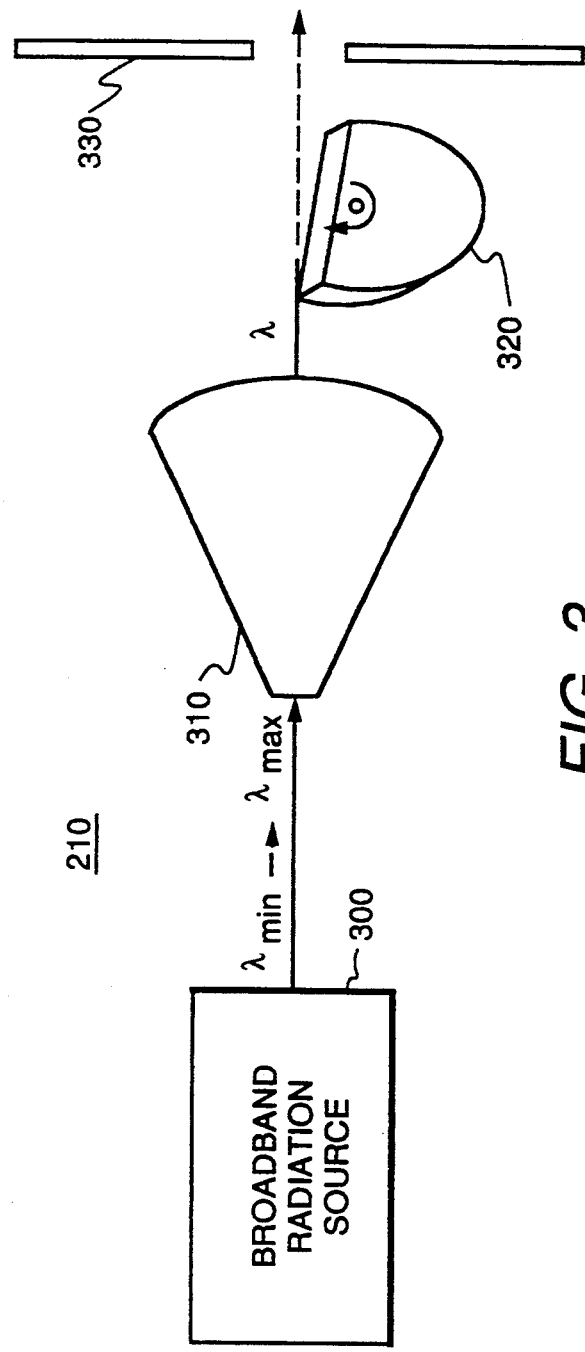
FIG. 3 is a block diagram of an embodiment of the pulsed EMR source of FIG. 2 used to generate radiation directed at the surface of said sample.

FIG. 3 is a detailed schematic illustration of one embodiment of pulsed EMR source 210. EMR source 210 includes a broadband radiation source 300 which sends radiation of an array of wavelengths $\lambda_{min} - > \lambda_{max}$ to a monochromator means 310. Monochromator means 310 propagates a small selected band of radiation wavelengths $\lambda$ between $\lambda_{min} - > \lambda_{max}$. An alternative embodiment of the invention uses a tunable laser, capable of radiating a selected wavelength as the radiation source. The monochromatic light enters a chopping means 320 where the light beam is interrupted mechanically, as by a rotating disk, at a selected frequency. The result is pulsed radiation having a wavelength $\lambda$ which exits pulsed EMR source 210 through an exit port 330. In an alternative embodiment, the chopping means 320 is situated between broadband radiation source 300 and monochromator means 310.

Figure 4:
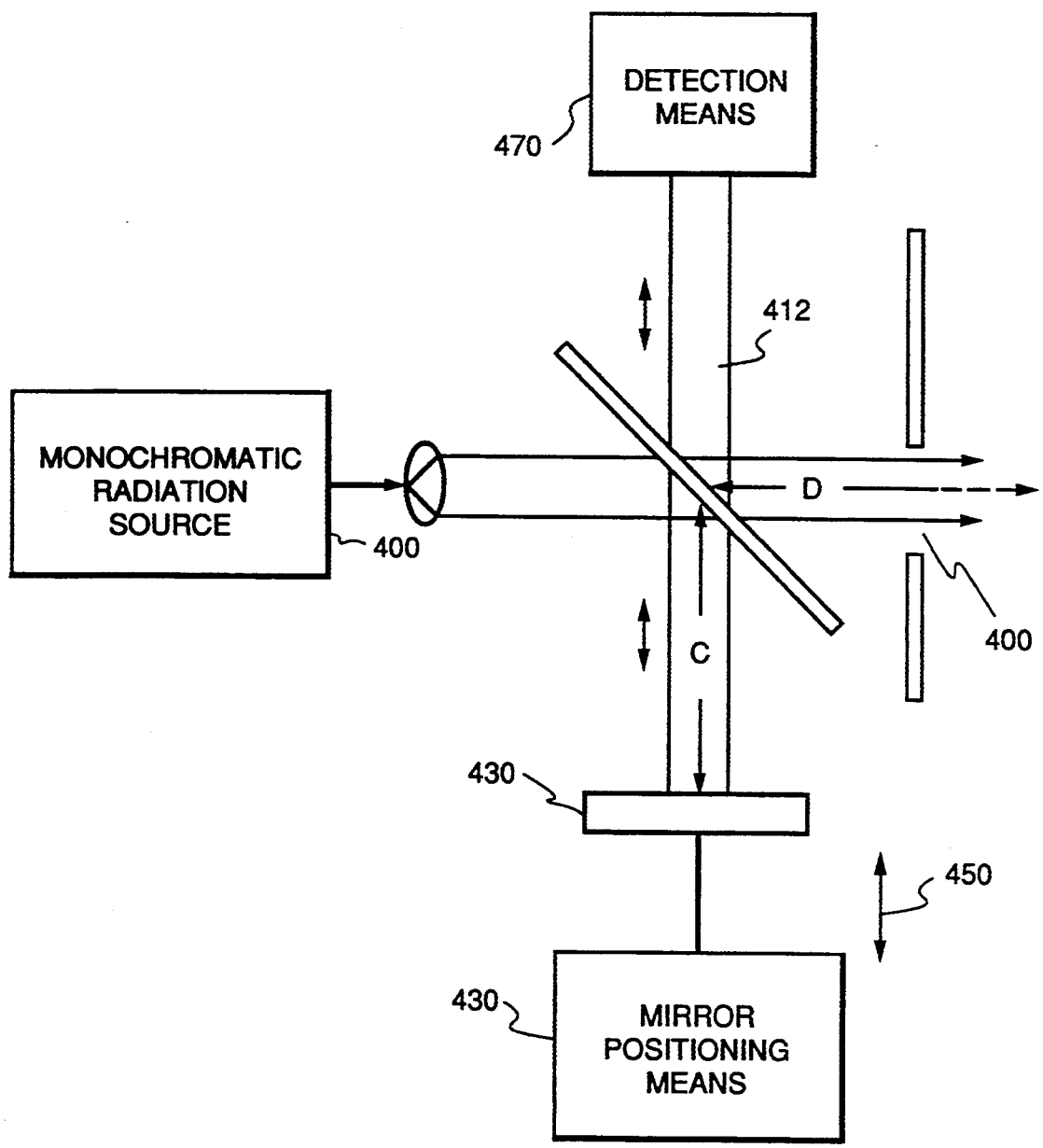
FIG. 4 is a block diagram of one embodiment of the interferometer means of FIG. 2 used to measure surface displacement caused by the absorption of radiation from a pulsed EMR source.

The pulsed radiation from pulsed EMR source 210 impinges upon the surface 110 of sample 100 of FIG. 1 where some fraction of the radiation is absorbed causing the temperature of the immediate area of the surface to rise. This rise in temperature in turn causes the material in the surface to expand. Since the radiation is pulsed, heating of surface 110 is periodic. This results in a periodic expansion and contraction of surface 110 at the pulsing frequency. This expansion and contraction is accurately measured with interferometer means 220 shown in greater detail in FIG. 4.

In interferometer means 220, a monochromatic radiation source 400 propagates radiation of a small band of wavelengths through a lens 405 to widen the beam which impinges upon a beam splitter means 410, such as a half-silvered mirror. The radiation is split into a first partially transmitted beam and a first partially reflected beam. The first partially reflected beam reflects off of a movable mirror 430 back to beam splitter 410 creating a second partially reflected beam and a second partially transmitted beam. In this embodiment, movable mirror 430 remains fixed, but can be moved by a mirror positioning means 440 along an axis 450 if desired. The first partially transmitted beam propagates through an exit port 460 of interferometer means 220 to impinge on the surface of the sample (not shown in FIG. 4) and a portion is reflected back from the sample surface to beam splitter 410, resulting in in a third partially reflected beam and a third partially transmitted beam. The third partially reflected beam is combined with the second partially transmitted beam to create a detection beam 412. If the distance C, between the beam splitter and mirror 430, and distance D, between the beam splitter and the sample surface, differ by an integral number of wavelengths of the monochromatic radiation source, radiation detected at a detection means 470 is in phase and combines constructively. Detection means 470 is designed to simultaneously sense intensities over a spatial region over time and may be, for example, a video camera. If, on the other hand, the distances C and D are not integral multiples of the wavelength, some destructive interference will occur. As the surface of the sample expands and contracts with time, responsive to the radiation from the first interferometer, the distances C and D will change with respect to each other. Consequently, the monochromatic radiation impinging on detection means 470 will be modulated at a frequency inversely proportional to the wavelength of pulsed EMR source 210 (FIG. 2) absorbed by sample 100 (FIG. 2) and at an amplitude commensurate with the degree of absorption.

The spectrum (i.e. absorption vs. wavelength) of sample 100 can be calculated by analyzing the modulated monochromatic radiation according to conventional optical spectroscopy techniques.

While several presently preferred embodiments of the novel spectroscopic imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A system for creating images representing chemical composition of a sample surface based upon the electromagnetic absorption spectra thereof, comprising:
    a) a pulsed electromagnetic radiation (EMR) source for irradiating a portion of said sample surface with a pulsed excitation beam of radiation of substantially a single wavelength at a time, and varying the wavelength for a plurality of selected wavelengths;
    b) interferometer means for creating and recording an interferogram when the portion of the sample is irradiated by the pulsed excitation beam, and a corresponding interferogram when the sample is not irradiated by the pulsed excitation beam for each of at least three distances between the interferometer means and said sample surface; and
    c) image formation means adapted to:
        1. create a surface roughness image of the portion of said sample surface from at least three interferograms recorded when the portion of the sample is irradiated by the pulsed excitation beam of a selected wavelength,
        2. create a surface roughness image of the portion of said sample surface from at least three interferograms recorded when the portion of the sample is not being irradiated by the pulsed excitation beam of the selected wavelength,
        3. determine a difference between the surface roughness images for the same selected excitation beam wavelength to create a difference image for each excitation beam wavelength indicating an amount of absorption of the given excitation beam wavelength, and
        4. calculate a absorption spectra of said sample surface from the difference images for a plurality of excitation beam wavelengths.

2. The system for creating images representing chemical composition of a sample surface of claim 1 further comprising means for comparing the absorption spectra of said sample surface with known absorption spectra to determine the chemical-type at a plurality of locations of the sample surface and construct a chemical-type map of said sample surface.

3. The system of claim 1 further comprising positioning means for moving said sample relative to the pulsed EMR source and the interferometer.

4. The system of claim 1, wherein the pulsed EMR source comprises:
    a1) a broadband radiation source for producing radiation having a plurality of wavelengths;
    a2) monochromator means for receiving the plurality of wavelengths and passing only a narrow band of said wavelengths; and
    a3) chopping means for interrupting the radiation, creating pulsed radiation.

5. The system of claim 1, wherein the interferometer means comprises:
    b1) a beam splitter for creating a partially transmitted and partially reflected beam from an incident beam;
    b2) a monochromatic radiation source for creating a radiation beam of a predetermined frequency for application to said sample surface through said beam splitter such that the beam splitter creates a first transmitted beam and a first reflected beam, the first transmitted beam being reflected off of said sample surface back to the beam splitter so as to be split by the beam splitter into a second transmitted and a second reflected beam;
    b3) a movable mirror for reflecting the first reflected beam back to the beam splitter so as to be split by the beam splitter into a third transmitted beam and a third reflected beam such that the third transmitted beam constructively and destructively interferes with the second reflected beam to create a detection beam; and
    b4) detection means for sensing the detection beam and interferogram indicating changes in distance between the interferometer means and a plurality of points on said sample surface versus time providing spatially resolved information from the irradiated portion of said sample surface.

6. The system of claim 5, wherein the image formation means includes means for generating images of said sample surface from the detected changes in distances obtained by said detection means in response to the pulsed radiation generated by the pulsed EMR source.

7. The system of claim 3, wherein the pulsed EMR source comprises means for generating radiation at a wavelength in one of the group of wavelengths consisting of: infra-red wavelengths, visible light wavelengths and ultra-violet wavelengths.

8. The system of claim 1, wherein the pulsed electromagnetic radiation (EMR) source comprises a laser.

9. The system of claim 1, wherein the pulsed EMR source comprises:
- a1) a tunable laser for creating radiation of substantially one selected wavelength; and
- a2) chopping means for interrupting the radiation, so as to create pulsed radiation.

10. The system of claim 1 further including an output device for creating an image indicating distribution of a desired chemical type from the absorption spectrum of the sample at said portion thereof.

11. A method of creating images representing chemical composition of a sample surface based upon the electromagnetic absorption spectra thereof, comprising the steps of:
- a) irradiating a portion of said sample surface with a pulsed excitation beam of radiation of a selected wavelength causing sample surface to absorb a portion of the pulsed excitation beam and expand periodically changing distance between the sample surface and a measurement point;
- b) measuring the distance between the sample surface and the measurement point when the sample is irradiated and when it is not irradiated using an interferometer;
- c) calculating a difference between the distance when irradiated and when not irradiated to indicate a degree of absorption of the excitation beam:
- d) repeating the steps of "a" through "c" for a plurality of different selected wavelengths: and
- e) creating absorption spectra for portions of said sample surface from the detected changes in distance indicating chemical composition of said sample surface.

12. The system of claim 12, wherein the step of measuring the distance comprises the steps of:
- b1) irradiating said sample with a monochromatic measurement beam;
- b2) mixing a return beam reflected from said sample with a portion of the measurement beam to create constructive and destructive interference in a mixed beam;
- b3) sampling the intensity of the mixed beam; and
- b4) calculating changes in distance between said sample surface and the measurement point from the sampled intensity.

13. The method of claim 11 further comprising, after the step of creating absorption spectra, the step of: comparing the absorption spectrum at a selected location on said sample surface to spectra of known chemical species to determine the chemical species whose spectrum most closely matches that of the selected location on the sample surface.

14. The method of claim 11 further comprising the steps of repeating steps "a" through "d" of claim 11 for a plurality of different locations on the sample surface to result in a chemical species map of the sample surface.

* * * * *